| United States Patent [19] | [11] | 4,350,706 |
|---|---|---|
| Brouwer et al. | [45] | Sep. 21, 1982 |

[54] UREA AND THIOUREA COMPOUNDS AND INSECTICIDAL COMPOSITIONS

[75] Inventors: Marius S. Brouwer; Arnoldus C. Grosscurt, both of Weesp, Netherlands

[73] Assignee: Duphar International Research B.V., Netherlands

[21] Appl. No.: 52,371

[22] Filed: Jun. 27, 1979

[30] Foreign Application Priority Data

Jul. 6, 1978 [NL] Netherlands .......................... 7807316

[51] Int. Cl.$^3$ ....................... C07C 127/22; A01N 9/20
[52] U.S. Cl. ..................................... 424/322; 564/23; 564/28; 564/44; 564/52; 564/47; 564/50; 564/53; 546/305; 260/465 D; 424/263; 263/304
[58] Field of Search ..................... 260/553 E; 424/322; 564/23, 28, 44, 52

[56] References Cited

U.S. PATENT DOCUMENTS

| 3,933,908 | 1/1976 | Wellinga et al. ................. 260/553 E |
| 3,992,553 | 11/1976 | Sirrenberg et al. .......... 260/553 E X |
| 4,005,223 | 1/1977 | Sirrenberg et al. ......... 260/553 E X |
| 4,041,177 | 8/1977 | Sirrenberg et al. ......... 260/553 E X |
| 4,068,002 | 1/1978 | Sirrenberg et al. ......... 260/553 E X |
| 4,123,449 | 10/1978 | Sirrenberg et al. ............... 564/44 X |
| 4,249,938 | 2/1981 | Takemoto et al. ................ 564/52 X |
| 4,260,411 | 4/1981 | Yoshida et al. .................... 564/52 X |

FOREIGN PATENT DOCUMENTS

| 2744169 | 4/1978 | Fed. Rep. of Germany ... 260/553 A |
| 7105350 | 10/1977 | Netherlands . |
| 2016010 | 9/1979 | United Kingdom ........... 260/553 A |

*Primary Examiner*—Thomas A. Waltz
*Attorney, Agent, or Firm*—Stevens, Davis, Miller & Mosher

[57] ABSTRACT

The invention relates to new urea and thiourea compounds as insecticides.

The compounds, after having been processed to compositions, can successfully be used to control insects in a dosage from 10 to 5000 g of active substance per hectare.

30 Claims, No Drawings

UREA AND THIOUREA COMPOUNDS AND INSECTICIDAL COMPOSITIONS

The invention relates to new urea and thiourea compounds and to a method of preparing the new compounds. The invention also relates to insecticidal compositions which contain the new compounds and to the use of these compositions for controlling insects.

In Applicants' Netherlands Patent Application No. 7105350 laid open to public inspection, benzoylureas are described having insecticidal activity. One compound mentioned in this patent application is N-(2,6-dichlorobenzoyl)-N'-[4-(4-chlorophenoxy)phenyl]urea of the formula below in which $R_1$ and $R_2$ are chlorine atoms.

These and related compounds have an interesting insecticidal activity, as appears from the results below against larvae of Pieris brassicae.

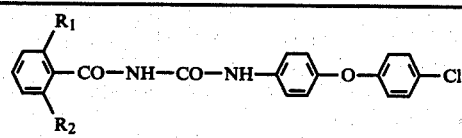

| Compound | | conc. in mg of active subst. per liter. | | | | |
|---|---|---|---|---|---|---|
| $R_1$ | $R_2$ | 100 | 30 | 10 | 3 | 1 |
| Cl | Cl | + | ± | − | | |
| H | Cl | + | + | + | ± | − |

The meanings of the symbols are as follows:
+ = 90-100% mortality
± = 50-90% mortality
− = <50% mortality It has surprisingly been found that the corresponding benzyloxy compounds as well as related compounds have considerably stronger insecticidal properties than the known compound. This is illustrated by the results stated in the following table which have been obtained by also determining the activity against larvae of Pieris brassicae;

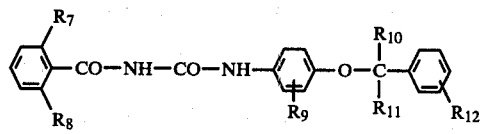

| Compound | | conc. in mg of active subst. per liter | | | | | | |
|---|---|---|---|---|---|---|---|---|
| $R_1$ | $R_2$ | 100 | 30 | 10 | 3 | 1 | 0.3 | 0.1 |
| Cl | Cl | + | + | ± | − | | | |
| H | CL | + | + | + | + | + | + | ± |
| F | F | + | + | + | + | + | + | + |

The present invention is therefore characterized by new urea and thiourea compounds of the general formula $R_1$—CX—NH—CY—NR$_2$—R$_3$—Z—R$_4$—R$_5$, wherein $R_1$ is a phenyl group, a pyridyl-3 group, or a pyridyl-4 group, which groups are substituted in the 2-position with respect to the CX-function with a halogen atom, an alkyl group having 1 or 2 carbon atoms, or a nitro group, and which group in the 6-position with respect to the CX-function may be substituted with a halogen atom or an alkyl group having 1 or 2 carbon atoms, $R_2$ is a hydrogen atom, a hydroxy group or a substituted or non-substituted alkyl group having 1 to 6 carbon atoms, $R_3$ is a p-phenylene group or a heteroarylene group having 1 or 2 nitrogen atoms, which groups may be substituted with 1 or 2 substituents selected from the group consisting of a halogen atom and an alkyl group or alkoxy group having 1 to 4 carbon atoms and possibly substituted with halogen, $R_4$ is an alkylene group, alkenylene group or alkylidene group having 1 to 4 carbon atoms, or a cycloalkylene group or cycloalkylidene group having 5 or 6 carbon atoms, which groups may be substituted with 1 or 2 substituents selected from the group consisting of a halogen atom, an alkyl group having 1 to 20 carbon atoms and substituted or not substituted with halogen or hydroxy, a phenyl group, a cyano group, an alkoxycarbonyl group having 2 to 6 carbon atoms, a hydroxyimino group, an alkoxyimino group having 1 to 6 carbon atoms, or an alkenyl group or alkynyl group having 1 to 6 carbon atoms, $R_5$ is a phenyl group or a heteroaryl group having 1 to 3 hetero atoms selected from the group of N, O and S, which groups may be substituted with 1, 2 or 3 substituents selected from the group consisting of a halogen atom, a nitro group, a cyano group and an alkyl group, alkenyl group, alkoxy group, alkenyloxy group, alkylthio group and alkylsulphonyl group having 1 to 6 carbon atoms and possibly substituted with halogen, X and Y are an oxygen atom or sulphur atom, and Z is an oxygen atom, a sulphur atom, a sulphonyl group, a sulphinyl group, an imino group or an alkylimino group having 1 to 4 carbon atoms, or wherein Z and $R_4$ together form an alkylidene amino group having 1 to 6 carbon atoms.

These compounds have an interesting insecticidal activity as will become apparent from the examples.

Of the above-mentioned compounds, generally those compounds prove to have a very large insecticidal activity which correspond to the formula:

wherein $R_7$ and $R_8$ or both are fluorine atoms, or $R_7$ is a hydrogen atom and $R_8$ a chlorine atom or a methyl group, $R_9$ represents from 0 to 2 substituents selected from the group consisting of a halogen atom and an alkyl group having 1 to 4 carbon atoms possibly substituted with halogen $R_{10}$ and $R_{11}$ are equal or different and represent a hydrogen atom, an alkyl group having 1 to 20 carbon atoms and substituted or not substituted with halogen or hydroxy, a phenyl group, a cyano group, or an alkenyl group or alkynyl group having 1 to 6 carbon atoms, and $R_{12}$ is a hydrogen atom or 1–2 substituents in the 3 and/or 4 position, selected from the group consisting of a halogen atom and an alkyl having 1 to 6 carbon atoms possibly substituted with halogen.

Of these latter compounds, particularly those compounds are excellently suitable which, in addition to a high insecticidal activity, have a wide activity spectrum, that is to say have a high activity against a large number of different insects, for example, caterpillars, larvae of flies and mosquitos and larvae of beetles. These excellently suitable compounds generally fall under the following formula

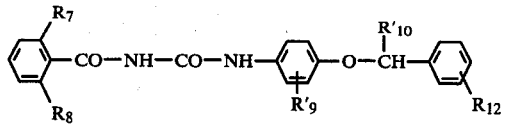

wherein $R_7$, $R_8$ and $R_{12}$ having the above-mentioned meanings, $R_9'$ is a hydrogen atom, or 1 or 2 chlorine atoms, or 1 or 2 alkyl groups having 1 to 4 carbon atoms in the 3-position or in the 3- and 5-positions with respect to the NH function, and $R_{10}'$ is a hydrogen atom or an alkyl group having 1 to 20 carbon atoms and substituted or not substituted with halogen, a phenyl group or an alkenyl group or alkynyl group having 1 to 6 carbon atoms.

Of the compounds represented by the latter formula are comparatively most effective compounds of the formula

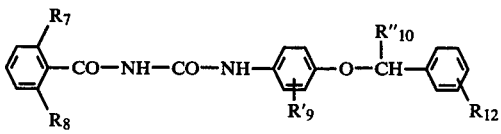

wherein $R_7$, $R_8$, $R_9'$ and $R_{12}$ have the above-mentioned meanings, and $R''_{10}$ is an alkyl group having 1 to 20 carbon atoms and substituted or not substituted with halogen, a phenyl group or an alkenyl group or alkynyl group having 1 to 6 carbon atoms.

Examples of very effective compounds having a wide activity spectrum are:

(1) N-(2,6-difluorobenzoyl)-N'-[4-(1-phenylethoxy)-phenyl]urea,
(2) N-(2-chlorobenzoyl)-N'-[4-(1-phenylethoxy)phenyl]urea,
(3) N -(2,6-difluorobenzoyl)-N'-[4-(1-phenylbutoxy)-phenyl]urea,
(4) N-(2-chlorobenzoyl)-N'-[4-(1-phenylbutoxy)phenyl]urea,
(5) N-(2,6-difluorobenzoyl)-N'-[4-(1-phenylheptyloxy)-phenyl]urea,
(6) N-(2-chlorobenzoyl)-N'-[4-(1-phenylheptyloxy)-phenyl]urea,
(7) N-(2,6-difluorobenzoyl)-N'-[4-(1-phenylpropoxy)-phenyl]urea,
(8) N-(2-chlorobenzoyl)-N'-[4-(1-phenylpropoxy)-phenyl]urea,
(9) N-(2-methylbenzoyl)-N'-[4-(1-phenylpropoxy)-phenyl]urea,
(10) N-(2,6-difluorobenzoyl)-N'-[4-{1-(4-chlorophenyl)ethoxy}-phenyl]urea,
(11) N-(2,6-difluorobenzoyl)-N'-(3,5-dichloro-4-benzyloxy-phenyl)urea,
(12) N-(2-chlorobenzoyl)-N'-(3,5-dimethyl-4-benzyloxyphenyl)urea,
(13) N-(2,6-difluorobenzoyl)-N'-(3,5-dimethyl-4-benzyloxyphenyl)urea,
(14) N-(2,6-difluorobenzoyl)-N'-[3,5-dichloro-4-(4-chlorobenzyloxy)phenyl]urea,
(15) N-(2,6-difluorobenzoyl)-N'-[3,5-dimethyl-4-(4-chlorobenzyloxy)phenyl]urea,
(16) N-(2-chlorobenzoyl)-N'-[4-(1-phenylisobutoxy)-phenyl]urea,
(17) N-(2-methylbenzoyl)-N'-[4-(1-phenylisobutoxy)-phenyl]urea,
(18) N-(2,6-difluorobenzoyl)-N'-[4-(1-phenylisobutoxy)phenyl]urea,
(19) N-(2-methylbenzoyl)-N'-[4-(1-phenylheptyloxy)-phenyl]urea,
(20) N-(2-chlorobenzoyl)-N'-[4-(α-phenylbenzyloxy)-phenyl]urea,
(21) N-(2,6-difluorobenzoyl)-N'-[4-(α-phenylbenzyloxy)phenyl]urea,
(22) N-(2-chlorobenzoyl)-N'-[4-(1-phenyl-2,2,2-trifluoroethoxy)phenyl]urea,
(23) N-(2-methylbenzoyl)-N'-[4-(1-phenyl-2,2,2-trifluoroethoxy)phenyl]urea,
(24) N-(2,6-difluorobenzoyl)-N'-[4-(1-phenyl-2,2,2-trifluoroethoxy)phenyl]urea,
(25) N-(2-chlorobenzoyl)-N'-[4-(1-phenyl-2,2-dichloroethoxy)phenyl]urea,
(26) N-(2,6-difluorobenzoyl)-N'-[4-(1-phenyl-2,2,2-trichloroethoxy)phenyl]urea,
(27) N-(2,6-difluorobenzoyl)-N'-[4-(1-phenylisobuten-2-yloxy)phenyl]urea,
(28) N-(2-chlorobenzoyl)-N'-[4-(1-phenylpropyn-2-yloxy)phenyl]urea,
(29) N-(2-methylbenzoyl)-N'-[4-(1-phenylpropyn-2-yloxy)phenyl]urea,
(30) N-(2,6-difluorobenzoyl)-N'-[4-(1-phenylpropyn-2-yloxy)phenyl]urea,
(31) N-(2-chlorobenzoyl)-N'-(4-benzyloxyphenyl)urea,
(32) N-(2,6-difluorobenzoyl)-N'-(4-benzyloxyphenyl)urea,
(33) N-(2,6-difluorobenzoyl)-N'-(3-chloro-4-benzyloxyphenyl)urea,
(34) N-(2,6-difluorobenzoyl)-N'-(3-methyl-4-benzyloxyphenyl)urea,
(35) N-(2-chlorobenzoyl)-N'-[4-(4-chlorobenzyloxy)-phenyl]urea,
(36) N-(2,6-difluorobenzoyl)-N'-[4-(4-chlorobenzoyloxy)phenyl]urea,
(37) N-(2-chlorobenzoyl)-N'-[3-chloro-4-(1-phenylethoxy)phenyl]urea,
(38) N-(2,6-difluorobenzoyl)-N'-[3-chloro-4-(1-phenylethoxy)phenyl]urea,
(39) N-(2-chlorobenzoyl)-N'-[3-chloro-4-{1-(4-chlorophenyl)ethoxy}phenyl]urea,
(40) N-(2-methylbenzoyl)-N'-[3-chloro-4-{1-(4-chlorophenyl)ethoxy}phenyl]urea,
(41) N-(2,6-difluorobenzoyl)-N'-[3-chloro-4-{1-(4-chlorophenyl)ethoxy}phenyl]urea,
(42) N-(2-chlorobenzoyl)-N'-[3-methyl-4-(1-phenylethoxy)phenyl]urea,
(43) N-(2-methylbenzoyl)-N'-[3-methyl-4-(1-phenylethoxy)phenyl]urea,
(44) N-(2,6-difluorobenzoyl)-N'-[3-methyl-4-(1-phenylethoxy)phenyl]urea,
(45) N-(2,6-difluorobenzoyl)-N'-[3-methyl-4-{1-(4-chlorophenyl)ethoxy}phenyl]urea,
(46) N-(2-chlorobenzoyl)-N'-[3-methyl-4-{1-(4-chlorophenyl)ethoxy}phenyl]urea, and
(47) N-(2-chlorobenzoyl)-N'-[3-chloro-4-(1-phenylpropoxy)phenyl]urea.

Examples of other very active insecticidal compounds are:

(48) N-(2-methylbenzoyl)-N'-[4-(1-phenylethoxy)-phenyl]urea,
(49) N-(2-chlorobenzoyl)-N'-(3,5-dichloro-4-benzyloxyphenyl)urea,
(50) N-(2-chlorobenzoyl)-N'-(3-chloro-4-benzyloxyphenyl)urea,
(51) N-(2-chlorobenzoyl)-N'-(3-methyl-4-benzyloxyphenyl)urea,
(52) N-(2-methylbenzoyl)-N'-(3-methyl-4-benzyloxyphenyl)urea
(53) N-(2-chlorobenzoyl)-N'-(3-trifluoromethyl-4-benzyloxyphenyl)urea,
(54) N-(2-methylbenzoyl)-N'-(3-trifluoromethyl-4-benzyloxyphenyl)urea,
(55) N-(2,6-difluorobenzoyl)-N'-(3-trifluoromethyl-4-benzyloxyphenyl)urea,
(56) N-(2-chlorobenzoyl)-N'-[3-chloro-4-(4-chlorobenzyloxy)phenyl]urea,
(57) N-(2,6-difluorobenzoyl)-N'-[3-chloro-4-(4-chlorobenzyloxy)phenyl]urea,
(58) N-(2,6-difluorobenzoyl)-N'-[3-methyl-4-(4-chlorobenzyloxy)phenyl]urea,
(59) N-(2,6-difluorobenzoyl)-N'-[3-trifluoromethyl-4-(4-chlorobenzyloxy)phenyl]urea,
(60) N-(2-methylbenzoyl)-N'-[3-chloro-4-(1-phenylethoxy)phenyl]urea,
(61) N-(2-chlorobenzoyl)-N'-[3-trifluoromethyl-4-(1-phenylethoxy)phenyl]urea,
(62) N-(2,6-difluorobenzoyl)-N'-[3-trifluoromethyl-4-(1-phenylethoxy)phenyl]urea,
(63) N-(2-chlorobenzoyl)-N'-[3-trifluoromethyl-4-{1-(4-chlorophenyl)ethoxy}phenyl]urea,
(64) N-(2-methylbenzoyl)-N'-[3-trifluoromethyl-4-{1-(4-chlorophenyl)ethoxy}phenyl]urea,
(65) N-(2,6-difluorobenzoyl)-N'-[3-trifluoromethyl-4-{1-(4-chlorophenyl)ethoxy}phenyl]urea,
(66) N-(2-chlorobenzoyl)-N'-[4-(α-cyanobenzyloxy)phenyl]urea,
(67) N-(2,6-difluorobenzoyl)-N'-[4-(α-cyanobenzyloxy)phenyl]urea,
(68) N-(2,6-difluorobenzoyl)-N'-[4-(1-phenyl-2-hydroxypropoxy)phenyl]urea,
(69) N-(2-chlorobenzoyl)-N'-[4-(α,α-dimethylbenzyloxy)phenyl]urea,
(70) N-(2,6-difluorobenzoyl)-N'-[4-(α,α-dimethylbenzyloxy)phenyl]urea,
(117) N-(2,6-difluorobenzoyl)-N'-[4-(3-phenylpropoxy)phenyl]urea,
(143) N-(2,6-difluorothiobenzoyl)-N'-[4(1-phenylethoxy)phenyl]urea,
(148) N-(2,6-difluorobenzoyl)-N'-[4-(4-chlorobenzylthio)phenyl]urea,
(151) N-(2,6-difluorobenzoyl)-N'-[4-(1-phenylethylthio)phenyl]urea,
(190) N-(2,6-difluorobenzoyl)-N'-[5-(2-benzyloxy)-pyridyl]urea, and
(192) N-(2,6-difluorobenzoyl)-N'-[5-{2-(4-chlorobenzyl)oxy}pyridyl]urea, Examples of other new urea and thiourea compounds according to the invention are:

(71) N-(2,6-dichlorobenzoyl)-N'-[4-(4-chlorobenzyloxy)phenyl]urea,
(72) N-(2,6-diiodobenzoyl)-N'-[3-chloro-4-(4-chlorobenzyloxy)phenyl]urea,
(73) N-(2-methylbenzoyl)-N'-(3,5-dimethyl-4-benzyloxyphenyl)urea,
(74) N-(2-chlorobenzoyl)-N'-[3-methyl-4-(4-chlorobenzyloxy)phenyl]urea,
(75) N-(2-methylbenzoyl)-N'-[3-methyl-4-(4-chlorobenzyloxy)phenyl]urea,
(76) N-(2-chlorobenzoyl)-N'-[3-trifluoromethyl-4-(4-chlorobenzyloxy)phenyl]urea,
(77) N-(2-chlorobenzoyl)-N'-[3,5-dichloro-4-(4-chlorobenzyloxy)phenyl]urea,
(78) N-(2-chlorobenzoyl)-N'-[3,5-dimethyl-4-(4-chlorobenzyloxy)phenyl]urea,
(79) N-(2-methylbenzoyl)-N'-[3,5-dimethyl-4-(4-chlorobenzyloxy)phenyl]urea,
(80) N-(2-chlorobenzoyl)-N'-[3,5-dichloro-4-(4-nitrobenzyloxy)phenyl]urea,
(81) N-(2,6-difluorobenzoyl)-N'-[3,5-dichloro-4-(4-nitrobenzyloxy)phenyl]urea,
(82) N-(2-chlorobenzoyl)-N'-[4-(4-cyanobenzyloxy)phenyl]urea,
(83) N-(2,6-difluorobenzoyl)-N'-[4-(4-cyanobenzyloxy)phenyl]urea,
(84) N-(2-chlorobenzoyl)-N'-[3-chloro-4-(4-cyanobenzyloxy)phenyl]urea,
(85) N-(2-methylbenzoyl)-N'-[3-chloro-4-(4-cyanobenzyloxy)phenyl]urea,
(86) N-(2,6-difluorobenzoyl)-N'-[3-chloro-4-(4-cyanobenzyloxy)phenyl]urea,
(87) N-(2-chlorobenzoyl)-N'-[3,5-dichloro-4-(4-cyanobenzyloxy)phenyl]urea,
(88) N-(2,6-difluorobenzoyl)-N'-[3,5-dichloro-4-(4-cyanobenzyloxy)phenyl]urea,
(89) N-(2-chlorobenzoyl)-N'-[4-(4-fluorobenzyloxy)phenyl]urea,
(90) N-(2,6-difluorobenzoyl)-N'-[4-(4-fluorobenzyloxy)phenyl]urea,
(91) N-(2-chlorobenzoyl)-N'-[4-(4-trifluoromethylbenzyloxy)phenyl]urea,
(92) N-(2,6-difluorobenzoyl)-N'-[4-(4-trifluoromethylbenzyloxy)phenyl]urea,
(93) N-(2-chlorobenzoyl)-N'-[3-methyl-4-(4-trifluoromethylbenzyloxy)phenyl]urea,
(94) N-(2,6-difluorobenzoyl)-N'-[3-methyl-4-(4-trifluoromethylbenzyloxy)phenyl]urea,
(95) N-(2-chlorobenzoyl)-N'-[4-(4-methylbenzyloxy)phenyl]urea,
(96) N-(2,6-difluorobenzoyl)-N'-[4-(4-methylbenzyloxy)phenyl]urea,
(97) N-(2-bromobenzoyl)-N'-[4-(1-phenylethoxy)phenyl]urea,
(98) N-(2-nitrobenzoyl)-N'-[4-(1-phenylethoxy)phenyl]urea,
(99) N-(2-chloro-6-fluorobenzoyl)-N'-[4-(1-phenylethoxy)phenyl]urea,
(100) N-(2,6-dichlorobenzoyl)-N'-[4-(1-phenylheptyloxy)phenyl]urea,
(101) N-(2-methylbenzoyl)-N'-[3-trifluoromethyl-4-(1-phenylethoxy)phenyl]urea,
(102) N-(2-chlorobenzoyl)-N'-[4-{1-(4-chlorophenyl)ethoxy}phenyl]urea,
(103) N-(2-chlorobenzoyl)-N'-{4-[1-(4-trifluoromethylphenyl)ethoxy}phenyl]urea,
(104) N-(2,6-difluorobenzoyl)-N'-[4-{1-(4-trifluoromethylphenyl)ethoxy}phenyl]urea,
(105) N-(2-chlorobenzoyl)-N'-[4-{1-(3-trifluoromethylphenyl)ethoxy}phenyl]urea,
(106) N-(2,6-difluorobenzoyl)-N'-[4-{1-(3-trifluoromethylphenyl)ethoxy}phenyl]urea, (107) N-(2-chlorobenzoyl)-N'-[4-{1-(4-trifluoromethylphenyl)pentyloxy}phenyl]urea,
(108) N-(2,6-difluorobenzoyl)-N'-[4-{1-(4-trifluoromethylphenyl)pentyloxy}phenyl]urea,
(109) N-(2-chlorobenzoyl)-N'-[4-(1-phenyl-2,2,2-trichloroethoxy)phenyl]urea,
(110) N-(2-chlorobenzoyl)-N'-[4-(α-ethoxycarbobenzyloxy)phenyl]urea,
(111) N-(2,6-difluorobenzoyl)-N'-[4-(α-ethoxycarbobenzyloxy)phenyl]urea,
(112) N-(2-methylbenzoyl)-N'-[4-(α-cyanobenzyloxy)phenyl]urea,
(113) N-(2-chlorobenzoyl)-N'-[4-(1-phenylisobuten-2-yloxy)phenyl]urea,
(114) N-(2-chlorobenzoyl)-N'-[4-(1-phenyl-2-hydroxypropoxy)phenyl]urea,
(115) N-(2-methylbenzoyl)-N'-[4-(1-phenyl-2-hydroxypropoxy)phenyl]urea,
(116) N-(2-chlorobenzoyl)-N'-[4-(3-phenylpropoxy)phenyl]urea,
(118) N-(2-methylbenzoyl)-N'-[4-(α,α-dimethylbenzyloxy)phenyl]urea,
(119) N-(2-chlorobenzoyl)-N'-[4-(1,1-dimethyl-2-phenylethoxy)phenyl]urea,
(120) N-(2-methylbenzoyl)-N'-[4-(1,1-dimethyl-2-phenylethoxy)phenyl]urea,
(121) N-(2,6-difluorobenzoyl)-N'-[4-(1,1-dimethyl-2-phenylethoxy)phenyl]urea,
(122) N-(2-chlorobenzoyl)-N'-[4-(2,2-diethyl-2-phenylethoxy)phenyl]urea,
(123) N-(2-methylbenzoyl)-N'-[4-(2,2-diethyl-2-phenylethoxy)phenyl urea,
(124) N-(2,6-difluorobenzoyl)-N'-[4-(2,2-diethyl-2-phenylethoxy)phenyl]urea,
(125) N-(2-chlorobenzoyl)-N'-[4-(2-methyl-2-phenylethoxy)phenyl]urea,
(126) N-(2-methylbenzoyl)-N'-[4-(2-methyl-2-phenylethoxy)phenyl]urea,
(127) N-(2,6-difluorobenzoyl)-N'-[4-(2-methyl-2-phenylethoxy)phenyl]urea,
(128) N-(2-chlorobenzoyl)-N'-[4-(1-ethyl-2-phenylethoxy)phenyl]urea,
(129) N-(2-methylbenzoyl)-N'-[4-(1-ethyl-2-phenylethoxy)phenyl]urea,
(130) N-(2,6-difluorobenzoyl)-N'-[4-(1-ethyl-2-phenylethoxy)phenyl]urea,
(131) N-(2-chlorobenzoyl)-N'-[4-(1-phenylcyclohexyloxy)phenyl]urea,
(132) N-(2-methylbenzoyl)-N'-[4-(1-phenylcyclohexyloxy)phenyl]urea,
(133) N-(2,6-difluorobenzoyl)-N'-[4-(1-phenylcyclohexyloxy)phenyl]urea,
(134) N-(2-chlorobenzoyl)-N'-[4-(2-phenyl-2-hydroxyiminoethoxy)phenyl]urea,
(135) N-(2,6-difluorobenzoyl)-N'-[4-(2-phenyl-2-hydroxyiminoethoxy)phenyl]urea,
(136) N-(2-chlorobenzoyl)-N'-[4-{2-(4-chlorophenyl)-2-hydroxy-iminoethoxy}phenyl]urea,
(137) N-(2,6-difluorobenzoyl)-N'-[4-{2-(4-chlorophenyl)-2-hydroxy-iminoethoxy}phenyl]urea,
(138) N-(2-chlorobenzoyl)-N'-[4-{2-(4-chlorophenyl)-2-methoxy-iminoethoxy}phenyl]urea,
(139) N-(2,6-difluorobenzoyl)-N'-[4-{2-(4-chlorophenyl)-2-methoxy-iminoethoxy}phenyl]urea,
(140) N-(2-chlorobenzoyl)-N'-[4-{2-(4-chlorophenyl)-2-butoxy-iminoethoxy}phenyl]urea,
(141) N-(2,6-difluorobenzoyl)-N'-[4-{2-(4-chlorophenyl)-2-butoxy-iminoethoxy}phenyl]urea,
(142) N-(2-chlorothiobenzoyl)-N'-[4-(1-phenylethoxy)phenyl]urea,
(144) N-(2-chlorothiobenzoyl)-N'-[4-(1-phenylethoxy)phenyl]thiourea,
(145) N-(2,6-difluorothiobenzoyl)-N'-[4-(1-phenylethoxy)phenyl]thiourea,
(146) N-(2-chlorobenzoyl)-N'-[4-(4-chloro-benzylthio)phenyl]urea,
(147) N-(2-fluorobenzoyl)-N'-[4-(4-chlorobenzylthio)phenyl]urea,
(149) N-(2-chlorobenzoyl)-N'-[4-(1-phenylethylthio)phenyl]urea,
(150) N-(2-methylbenzoyl)-N'-[4-(1-phenylethylthio)phenyl]urea,
(152) N-(2-chlorobenzoyl)-N'-[4-{1-(4-chlorophenyl)ethylthio}phenyl]urea,
(153) N-(2,6-difluorobenzoyl)-N'-[4-{1-(4-chlorophenyl)ethylthio}phenyl]urea,
(154) N-(2-chlorobenzoyl)-N'-[3-chloro-4-(1-phenylethylthio)phenyl]urea,
(155) N-(2,6-difluorobenzoyl)-N'-[3-chloro-4-(1-phenylethylthio)phenyl]urea,
(156) N-(2-chlorobenzoyl)-N'-[3-chloro-4-{1-(4-chlorophenyl)ethylthio}phenyl]urea,
(157) N-(2,6-difluorobenzoyl)-N'-[3-chloro-4-{1-(4-chlorophenyl)ethylthio}phenyl]urea,
(158) N-(2-chlorobenzoyl)-N'-(4-benzylsulphonylphenyl)urea,
(159) N-(2-chlorobenzoyl)-N'-[4-{1-(4-chlorophenyl)ethylsulphonyl}phenyl]urea,
(160) N-(2,6-difluorobenzoyl)-N'-[4-{1-(4-chlorophenyl)ethylsulphonyl}phenyl]urea,
(161) N-(2-chlorobenzoyl)-N'-[4-{1-(4-trifluoromethylphenyl)ethylthio}phenyl]urea,
(162) N-(2-methylbenzoyl)-N'-[4-{1-(4-trifluoromethylphenyl)ethylthio}phenyl]urea,
(163) N-(2,6-difluorobenzoyl)-N'-[4-{1-(4-trifluoromethylphenylethylthio}phenyl]urea,
(164) N-(2-chlorobenzoyl)-N'-[3,5-dichloro-4-(1-phenylethylthio)phenyl]urea,
(165) N-(2,6-difluorobenzoyl)-N'-[3,5-dichloro-4-(1-phenylethylthio)phenyl]urea,
(166) N-(2-chlorobenzoyl)-N'-(3-chloro-4-benzylsulphonylphenyl)urea,
(167) N-(2,6-difluorobenzoyl)-N'-(3-chloro-4-benzoylsulphonylphenyl)urea,
(168) N-(2-chlorobenzoyl)-N'-[3,5-dichloro-4-(1-phenylethylsulphonyl)ethyl]urea,
(169) N-(2,6-difluorobenzoyl)-N'-[3,5-dichloro-4-(1-phenylethylsulphonyl)ethyl]urea,
(170) N-(2-chlorobenzoyl)-N'-(3-chloro-4-benzylthiophenyl)urea,
(171) N-(2,6-difluorobenzoyl)-N'-(3-chloro-4-benzylthiophenyl)urea,
(172) N-(2-chlorobenzoyl)-N'-[3,5-dichloro-4-{1-(4-chlorophenyl)ethylthio}phenyl]urea,
(173) N-(2,6-difluorobenzoyl)-N'-[3,5-dichloro-4-{1-(4-chlorophenyl)ethylthio}phenyl]urea,
(174) N-(2-chlorobenzoyl)-N'-[4-{1-(3-trifluoromethylphenyl)ethylthio}phenyl]urea,
(175) N-(2,6-difluorobenzoyl)-N'-[4-{1-(3-trifluoromethylphenyl)ethylthio}phenyl]urea,
(176) N-(2-chlorobenzoyl)-N'-[4-(1-phenylethylsulphonyl)phenyl]urea,
(177) N-(2,6-difluorobenzoyl)-N'-[4-(1-phenylethylsulphonyl)phenyl]urea,
(178) N-(2-chlorobenzoyl)-N'-[3,5-dichloro-4-{1-(4-chlorophenyl)ethylsulphonyl}phenyl]urea, (179) N-(2,6-difluorobenzoyl)-N'-[3,5-dichloro-4-{1-(4-chlorophenyl)ethylsulphonyl}phenyl]urea,
(180) N-(2-chlorobenzoyl)-N'-[3-chloro-4-{1-(4-trifluoromethylphenyl)ethylthio}phenyl]urea,
(181) N-(2,6-difluorobenzoyl)-N'-[3-chloro-4-{1-(4-trifluoromethylphenyl)ethylthio}phenyl]urea,
(182) N-(2-chlorobenzoyl)-N'-[4-(N-methyl-N-benzylimino)phenyl]urea,
(183) N-(2,6-difluorobenzoyl)-N'-[4-(N-methyl-N-benzylimino)phenyl]urea,
(184) N-(2-chlorobenzoyl)-N'-[4-(α-cyanobenzylimino)phenyl]urea,
(185) N-(2,6-difluorobenzoyl)-N'-[4-(α-cyanobenzylimino)phenyl]urea,
(186) N-(2-chlorobenzoyl)-N'-(4-benzylideneaminophenyl)urea,
(187) N-(2,6-difluorobenzoyl)-N'-(4-benzylideneaminophenyl)urea,
(188) N-(3-chloroisonicotinoyl)-N'-[4-(4-chlorobenzyloxy)phenyl]urea,
(189) N-(2-chlorobenzoyl)-N'-[5-(2-benzyloxy)pyridyl]urea,
(191) N-(2-chlorobenzoyl)-N'-[5-{2-(4-chlorobenzoyl)oxy}pyridyl]urea,
(193) N-(3-chloroisonicotinoyl)-N'-[4-(1-phenylethoxy)phenyl]urea,
(194) N-(3-chloroisonicotinoyl)-N'-[4-{1-(4-chlorophenyl)ethoxy}phenyl]urea,
(195) N-(3-chloroisonicotinoyl)-N'-[3,5-dichloro-4-(1-phenylthio)phenyl]urea,
(196) N-(2,6-difluorobenzoyl)-N'-[4-(4-pyrodylmethoxy)phenyl]urea,
(197) N-(2,6-difluorobenzoyl)-N'-[4-{1-(4-pyridyl)ethoxy}phenyl]urea,
(198) N-(2-chlorobenzoyl)-N'-[4-{1-(4-pyridyl)ethoxy}phenyl]urea,
(199) N-(2-methylbenzoyl)-N'-[4-{1-(4-pyridyl)ethoxy}phenyl]urea,
(200) N-(2-chlorobenzoyl)-N'-[4-(2-thienylmethoxy)phenyl]urea,
(201) N-(2-methylbenzoyl)-N'-[4-(2-thienylmethoxy)phenyl]urea,
(202) N-(2,6-difluorobenzoyl)-N'-[4-(2-thienylmethoxy)phenyl]urea,
(203) N-(2-chlorobenzoyl)-N'-[4-(2-thienylmethylthio)phenyl]urea,
(204) N-(2-methylbenzoyl)-N'-[4-(2-thienylmethylthio)phenyl]urea,
(205) N-(2,6-difluorobenzoyl)-N'-[4-(2-thenylmethylthio)phenyl]urea,
(206) N-(2,6-difluorobenzoyl)-N'-[3-chloro-4-(2-thienylmethoxy)phenyl]urea,
(207) N-(2-chlorobenzoyl)-N'-[3-chloro-4-(2-thienylmethoxy)phenyl]urea,
(208) N-(2-methylbenzoyl)-N'-[3-chloro-4-(2-thienylmethoxy)phenyl]urea,
(209) N-(2-chlorobenzoyl)-N'-[4-(4-trifluoromethoxybenzyloxy)phenyl]urea,
(210) N-(2,6-difluorobenzoyl)-N'-[4-(4-trifluoromethoxybenzyloxy)phenyl]urea,
(211) N-(2-chlorobenzoyl)-N'-[3-methyl-4-(4-trifluoromethoxybenzyloxy)]phenyl urea,
(212) N-(2,6-difluorobenzoyl)-N'-[3-methyl-4-(4-trifluoromethoxybenzyloxy)phenyl]urea,
(213) N-(2-chlorobenzoyl)-N'-[3-trifluoromethyl-4-(4-trifluoromethoxybenzyloxy)phenyl]urea,
(214) N-(2,6-difluorobenzoyl)-N'-[3-trifluoromethyl-4-(4-trifluoromethoxybenzyloxy)phenyl]urea,
(215) N-(2-chlorobenzoyl)-N'-[3-chloro-4-(4-trifluoromethoxybenzyloxy)phenyl]urea,
(216) N-(2,6-difluorobenzoyl)-N'-[3-chloro-4-(4-trifluoromethoxybenzyloxy)phenyl]urea,
(217) N-(2,6-difluorobenzoyl)-N'-[4-(4-methoxybenzyloxy)phenyl]urea,
(218) N-(2-chlorobenzoyl)-N'-[4-(4-methoxybenzyloxy)phenyl]urea,
(219) N-(2,6-difluorobenzoyl)-N'-[4-(3-pyridylmethyl)phenyl]urea,
(220) N-(2-chlorobenzoyl)-N'-[4-(3-pyridylmethyl)phenyl]urea,
(221) N-(2-methylbenzoyl)-N'-[4-(3-pyridylmethyl)phenyl]urea,
(222) N-(2,6-difluorobenzoyl)-N'-[3-chloro-4-(1-phenylpropoxy)phenyl]urea,
(223) N-(2-methylbenzoyl)-N'-[3-chloro-4-(1-phenylpropoxy)phenyl]urea.

The compounds of the invention may be used for the control of mites and insects in agriculture and horticulture, in forests and surface water, as well as for the protection of textile against attack by, for example, moths and carpet beetles, and against insects in stocks, for example in stored cereals.

The substances according to the invention may also be used for the control of insects living in the manure of warm-blooded animals, for example cows, pigs and hens. For this application the active compounds may be administered orally to the animals, for example, mixed through the food, so that they will land in the manure after some time ("through-feeding").

The compounds according to the invention are particularly active against larvae and ova of insects such as flies, mosquitos, beetles and butterflies.

In principle the compounds may be used against all insects mentioned in Pestic. Sci., 9, 373–386 (1978).

For practical applications the compounds are usually processed to form compositions. In such compositions the active substance is mixed with solid carrier material or dissolved or dispersed in liquid carrier material, if desired in combination with auxiliary substances, such as emulsifiers, wetting agents, dispersing agents and stabilisers.

Examples of compositions of the invention are aqueous solutions and dispersions, oil solutions and oil dispersions, solutions in organic solvents, pastes dusting pow-ders, dispersible powders, miscible oils, granules, pellets, invert emulsions, aerosol compositions and fumigating candles.

Dispersible powders, pastes and miscible oils are compositions in concentrated form which are diluted prior to or during use.

The invert emulsions and solutions in organic solvents are mainly used in air applications, namely when large areas are to be treated with a comparatively small quantity of composition. The invert emulsion may be prepared in the spraying apparatus shortly prior to or even during spraying by emulsifying water in an oil solution or an oil dispersion of the active substance. The solutions of the active substance in organic solvents may be provided with a phytotoxicity-reducing substance, for example wool fat, wool fat acid or wool fat alcohol.

A number of compositions will now be described by way of example.

Granular compositions are prepared, for example, by taking up the active substance in a solvent or dispersing it in a diluent and impregnating the resulting solution/suspension, if desired in the presence of a binder, on granular carrier material such as porous granules (for example, pumice and attaclay), mineral nonporous granules (sand or ground marlow), organic granules (for example dried coffee grounds, cut tobacco stems and ground corncobs). A granular composition may also be manufactured by compressing the active substance together with powdered minerals in the presence of lubricants and binders and disintegrating the compressed product to the desired grain size and sieving it. Granular compositions can be prepared differently by mixing the active substance in powder form with powdered fillers and then glomulating the mixture with liquid to the desired particle size.

Dusting powders can be obtained by intimately mixing the active substance with an iner solid powdered carrier material, for example talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example, the lignin sulphonates of alkylnaphthalene sulphonates known for this purpose, preferably also 0.5 to 5 parts by weight of a wetting agent, for example fatty alcohol sulphates, alkylarylsulphonates, fatty acid condensation products, or polyoxyethylene compounds, and finally, if desired, other additives.

For the preparation of miscible oils the active compound is dissolved in a suitable solvent which is preferably poorly water-miscible and one or more emulsifiers are added to the solution, Suitable solvents are, for example xylene, toluene, petroleum distillates which are rich in aromatics, for example solvent naphtha, distilled tar oil and mixtures of these liquids. As emulsifiers may be used, for example, polyoxyethylene compounds and/or alkylaryl sulphonates. The concentration of the active compound in these miscible oils is not restricted and may vary widely, for example, between 2 and 50% by weight.

In addition to a miscible oil a liquid and highly concentrated primary composition may be mentioned as a solution of the active substance in a readily water-miscible liquid, for example, a glycol or glycol ether, to which solution a dispersing agent and, if desired, a surface-active substance has been added. Upon dilution with water shortly before or during spraying an aqueous dispersion of the active substance is obtained.

An aerosol composition according to the invention is obtained in the usual manner by incorporating the active substance, if desired in a solvent, in a volatile liquid as the propellent gas, for example a mixture of chlorofluoro derivatives of methane and ethane, a mixture of lower hydrocarbons, dimethyl ether, or gases such as carbon dioxide, nitrogen and nitrous oxide.

Fumigating candles or fumigating powders, that is, compositions which while burning generate a pesticidal smoke, are obtained by taking up the active substance in a combustible mixture which may comprise, for example, as a fuel a sugar or a wood, preferably in the ground form, a substance to maintain combustion, for example ammonium nitrate or potassium chlorate and furthermore a substance to delay combustion, for example, kaolin, bentonite and/or colloidal silicic acid.

In addition to the above-mentioned ingredients the compositions may also comprise other substances with properties known for such application.

For example, a lubricant such as calcium stearate or magnesium stearate, may be added to a dispersible powder or a mixture to be granulated. "Adhesives", for example polyvinyl alcohol cellulose derivatives or other colloidal materials, such as casein, may also be added for example so as to improve the adhesion of the pesticide to the crop. Furthermore, a substance may be added so as to reduce the phytotoxicity of active substance, carrier material of auxiliary material, such as wool fat or wool fat alcohol.

Known pesticidal compounds may also be incorporated in the compositions according to the invention. As a result of this the activity spectrum of the composition is widened and synergism may occur.

The following known insecticidal, acaricidal, and fungicidal compounds are to be considered for use in such a combination.

Insecticides, for example:
1. organic chlorine compounds, for example 6,7,8,9,10,10-hexachloro-1,5,5a,6,9,9a-hexahydro-6,9-methano-2,4,3-benzo[e]-dioxathiepine 3-oxide;
2. carbamates, for example 2-dimethylamino-5,6-dimethyl pyrimidin-4-yl-dimethyl carbamate and 2-isopropoxy-phenylmethylcarbamate;
3. Di(m)ethyl phosphates, for example 2-chloro-2-diethylcarbamoyl-1-methylvinyl, 2-methoxycarbonyl-1-methylvinyl-2-chloro-1-1(2,4-dichlorophenyl)vinyl, and 2-chloro-1-1(2,4,5-trichlorophenyl)vinyl di(m)ethyl phosphate;
4. O,O-di(m)ethyl phosphorothioates, for example O(S)-2-methylthioethyl, S-2-ethylsulphinylethyl, S-2-(1-methylcarbamoylethylthio)ethyl, O-4-bromo-2,5-dichlorophenyl, O-3,5,6-trichloro-2-pyridyl, O-2-isopropyl-6-methylpyrimidin-4-yl, and O-4-nitrophenyl-O,O-di(m)ethylphosphorothioate;
5. O,O-di(m)ethyl phosphorodithioates, for example S-methylcarbamoylmethyl, S-2-ethylthioethyl, S-(3,4-dihydro-4-oxobenzo[d]-[1,2,3]-triazin-3-yl-methyl) S-1,2-di(ethoxycarbonyl)ethyl, S-6-chloro-2-oxobenzooxazolin-3-ylmethyl, and S-2,3-dihydro-5-methoxy-2-oxo-1,3,4-thiadizol-3-ylmethyl O,O-di(m)ethylphosphorodithioate;
6. Phosphonates, for example dimethyl 2,2,2-trichloro-1-hydroxyethyl phosphonate.
7. Natural and synthetic pyrethroids;
8. amidines, for example N'-(2-methyl-4-chlorophenyl)-N,N-dimethylformamidine; and
9. microbial insects, such as *Bacillus Thuringiensis*.

Acaricides, for example:
1. organic tin compounds, for example tricyclohexyltin hydroxide and di[tri-(2-methyl-2-phenylpropyl)tin-]oxide;
2. organic halogen compounds, for example isopropyl 4,4'-di-bromobenzilate, 2,2,2-trichloro-1,1-di(4-chlorophenyl) ethanol, and 2,4,5,4'-tetrachlorodiphenylsulfon; and furthermore: 3-chloro-α-ethoxyimino-2,6-dimethoxybenzyl benzoate and O,O-dimethyl S-methylcarbamoylmethyl phosphorothioate.

Fungicides, for example:
1. organic tin compounds, for example triphenyl tin hydroxide and triphenyl tin acetate;
2. alkylenebisdithiocarbamates, for example, zincethylenebisdithiocarbamate and manganese ethylenebisdithiocarbamate;

3. 1-acyl or 1-carbamoyl-N-benzimidazole (-2) carbamates and 1,2-bis(3-alkoxycarbonyl-2-thiureido)benzene; and furthermore, 2,4-dinitro-6-(2-octylphenylcrotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)benzimidazole, 5-butyl-2-ethylamino-6-methylpyrimidine-4-yl-dimethylsulphamate, 1-(4-chloro-phenoxy-3,3-dimethyl-1-(1,2,4-triazol-1-yl)2-butanone, α-(2-chlorophenyl)-α-(4-chlorophenyl5-pyrimidinemethanol, 1-(isoporpylcarbamoyl)-3-(3,5-dichlorophenyl)hydantoine, N-(1,1,2,2-tetrachloroethylthio)4-cyclohexene-1,2-carboximide, N-trichloromethylmercapto-4-cyclohexene-1,2-dicarboximide, and N-tridecyl-2,6-dimethylmorpholine.

The dosage of the composition of the invention desired for practical application will of course depend on various factors, for example, the application area, the active substance chosen, the form of the composition, the nature and the extent of the infestation and the weather conditions.

In general it holds that favourable results are achieved with a dose which corresponds to 10 to 5000 g of the active substance per hectare.

For the above-described "through-feeding" the active substance is mixed through the food in a quantity which is effective for insecticidal application.

The compounds according to the invention are new substances which can be prepared in a manner which is known per se for related compounds.

For example, the compounds according to the invention can be prepared by reacting a substituted amine of the general formula

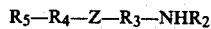
$$R_5—R_4—Z—R_3—NHR_2$$

wherein $R_2$, $R_3$, $R_4$ and $R_5$ and $Z$ have the above-mentioned meanings, with an isocyanate or isothiocyanate of the general formula $$R_1—CX—NCY,$$

wherein $R_1$, X and Y have the meanings also stated above.

The new compounds according to the invention wherein $R_2$ is a hydrogen atom can also be prepared by reacting a compound of the general formula

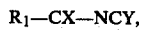
$$R_1—CX—NH_2,$$

with an isocyanate or isothiocyanate of the general formula

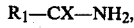
$$R_5—R_4—Z—R_3—NCY$$

in which formulae the symbols again have the above meanings. The above reactions are carried out in the presence of a solvent, for example, an aromatic hydrocarbon, a halogen-alkane or acetonitrile, at a reaction temperature between 0° C. and the boiling point of the solvent used.

Compounds according to the invention which satisfy the general formula

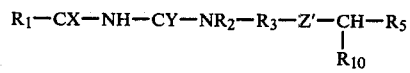
$$R_1—CX—NH—CY—NR_2—R_3—Z'—\underset{R_{10}}{\overset{|}{CH}}—R_5$$

wherein $R_1$, $R_2$, $R_3$, $R_5$, $R_{10}$, X and Y have the above meanings and Z' is an oxygen atom, a sulphur atom or an imino group, can also be prepared by reacting a compound of the general formula $$R_1—CX—NH—CY—NR_2—R_3—Z'H$$

with a halogenide of the general formula

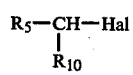
$$R_5—\underset{R_{10}}{\overset{|}{CH}}—Hal$$

wherein Hal is a halogen atom. This reaction is preferably carried out under the influence of a base in a polar organic solvent which is inert with respect to reaction components and final product. The reaction is carried out at a temperature between 0° C. and the boiling point of the solvent used. The reaction can also be produced in the presence of a catalytic quantity of a metal complex.

Although the above-described modes of preparation are the best suitable, the new compounds may alternatively be prepared in another manner, for example, as described in the above-mentioned Netherlands Patent Application No. 7105350.

The new compounds can also be prepared by a reaction of an aroylhalogenide with a urea or thiourea compound.

Another method of preparation consists in that an aroylamide or thioamide is first reacted with a strong base, for example, alkyllithium, after which the desired urea compound is synthesized by reacting the formed product either with an O-arylcarbamate or with successively an arylchloroformiate and an amine.

Compounds of the general formula

$$R_1—CX—NH—CY—NR_2—R_3—Z—R'_4—R_5$$

wherein $R_1$, $R_2$, $R_3$, $R_5$, X, Y and Z have the above meanings, and $R'_4$ is an alkylene group or alkylidene group having 1 to 4 carbon atoms which is substituted with a hydroxy-substituted alkyl group having 1 to 20 carbon atoms, can also be prepared by reduction of the corresponding carbonyl compound of the general formula

$$R_1—CX—NH—CY—NR_2—R_3—Z—R''_4—R_5$$

wherein $R''_4$ is an alkylene group or alkylidene group having 1 to 4 carbon atoms, which is substituted with an alkyl group having 1 to 20 carbon atoms and having a carbonyl group. This reduction may be carried out with a hydride, for example, sodium borohydride, in a suitable solvent or diluent, for example dilute sodium hydroxide solution. The reduction may also be produced catalytically with hydrogen gas under the influence of, for example, Raney nickel as a catalyst.

Compounds of the general formula

$$R_1—CX—NH—CY—NR_2—R_3—SO_2—R_4—R_5$$

wherein $R_1$, $R_2$, $R_3$, $R_4$, $R_5$, X and Y have the above meanings, can also be prepared by oxidation of the corresponding thio compound of the general formula

$$R_1-CX-NH-CY-NR_2-R_3-S-R_4-R_5.$$

This oxidation can be produced, for example, with a peroxy acid, for example, performic acid, or peracetic acid—formed in situ from acetic acid and hydrogen peroxide.

Compounds of the general formula

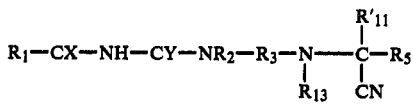

wherein
$R_1$, $R_2$, $R_3$, $R_5$, X and Y have the above meanings
$R_{13}$ is a hydrogen atom or an alkyl group having 1 to 4 carbon atoms, and
$R'_{11}$ is a hydrogen atom or an alkyl group having 1 to 5 carbon atoms,
are preferably prepared by reacting a substituted amine of the general formula

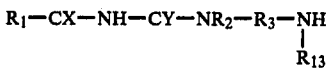

with a cyano hydrine or the general formula

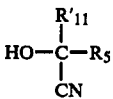

This reaction is usually carried out under the influence of a base in a suitable organic solvent, preferably at the boiling point of the solvent used.

Compounds of the general formula

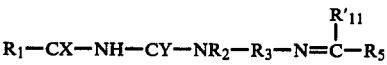

wherein $R_1$, $R_2$, $R_3$, $R_5$, $R'_{11}$, X and Y have the above meanings, are preferably prepared by reacting an amine of the general formula

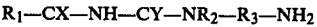

with an aldehyde or ketone of the general formula

This reaction is carried out in a suitable organic solvent, preferably at the boiling point of the solvent used.

The invention will now be described in more detail with reference to the following specific examples.

EXAMPLE 1

Preparation of N-(2-chlorobenzoyl)-N'-[4-(1-phenylethoxy)phenyl-]urea (2).

18.7 g of 2-chlorobenzoylisocyanate were added to 150 ml of a solution of 23.4 g of 4-(1-phenylethoxy)aniline in dry acetonitrile. After stirring at room temperature for a few hours, the crystalline precipitate was sucked off, washed with successively acetonitrile, ethanol and petroleum ether and dried in air. The desired product was obtained in a yield of 32.8 g; melting point 166°–167° C. The starting aniline was obtained from the corresponding nitro compound by hydrogenation with hydrogen under the influence of Raney nickel as a catalyst in alcohol as a solvent. α-Methylbenzyl-4-nitrophenyl ether was prepared from a reaction of 1-bromo-1-phenyl-ethane and 4-nitrophenol under the influence of anhydrous potassium carbonate in acetone as a solvent.

In a corresponding manner in which, if desired, dry diethyl ether was used as a solvent instead of acetonitrile, the following compounds were prepared: the numbers of the compounds correspond to the numbers used before in this specification.

| Comp. No. | Melt. pnt. | Comp. No. | Melt. pnt. |
|---|---|---|---|
| (1) | 167° C. | (107) | 156° C. |
| (3) | 180° C. | (108) | 163° C. |
| (4) | 152° C. | (109) | 143° C. |
| (5) | 151–153° C. | (110) | 155° C. |
| (6) | 134–136° C. | (111) | 140° C. |
| (7) | 190° C. | (112) | 158–161° C. |
| (8) | 150° C. | (113) | 133–137° C. |
| (9) | 136° C. | (116) | 150° C. |
| (10) | 189–191° C. | (117) | 168° C. |
| (11) | 215° C. | (118) | 192–195° C. |
| (12) | 168° C. | (119) | 117–122° C. |
| (13) | 163.5° C. | (120) | 81–84° C. |
| (14) | 204° C. | (121) | 125–130° C. |
| (15) | 184° C. | (122) | 172–174° C. |
| (16) | 158° C. | (123) | 140–145° C. |
| (17) | 135° C. | (124) | 150–151° C. |
| (18) | 181° C. | (125) | 140–143° C. |
| (19) | 104.5–106° C. | (126) | 158–162° C. |
| (20) | 216° C. | (127) | 142–144° C. |
| (21) | 211° C. | (128) | 107–110° C. |
| (22) | 160–161° C. | (129) | 120–125° C. |
| (23) | 130.5–133° C. | (130) | 130–133° C. |
| (24) | 164–165° C. | (131) | 232° C. |
| (25) | 137–148° C. | (132) | 206° C. |
| (26) | 188–189° C. | (133) | 218° C. |
| (27) | 156–157.5° C. | (134) | 209.5–211.5° C. |
| (31) | 177° C. | (135) | 210–212° C. |
| (32) | 204° C. | (136) | 197–199° C. |
| (33) | 193° C. | (137) | 210.5–212° C. |
| (34) | 176° C. | (138) | 181.5–184° C. |
| (35) | 190° C. | (139) | 167–168° C. |
| (36) | 214° C. | (140) | 140.5–143° C. |
| (37) | 163° C. | (141) | 144.5–146.5° C. |
| (38) | 190° C. | (146) | 196–197.5° C. |
| (39) | 206° C. | (147) | 175.5–176° C. |
| (40) | 174° C. | (148) | 189.5–191° C. |
| (41) | 195° C. | (149) | 170–171° C. |
| (42) |  | (150) | 136–137° C. |
| (43) | 144.5° C. | (151) | 162° C. |
| (44) | 170° C. | (152) | 193–194° C. |
| (45) | 166.5° C. | (153) | 185–185.5° C. |
| (46) | 161° C. | (154) | 158–158.5° C. |
| (48) | 165° C. | (155) | 176–176.5° C. |
| (49) | 229° C. | (156) | 180–183° C. |
| (50) | 206° C. | (157) | 180–181° C. |
| (51) | 165° C. | (158) | 234° C. |
| (52) | 166° C. | (159) | 220–226° C. |
| (53) | 205° C. | (160) | 219–221° C. |
| (54) | 187° C. | (161) | 198–199° C. |
| (55) | 190° C. | (162) | 169–170° C. |
| (56) | 212° C. | (163) | 202–203° C. |
| (57) | 234° C. | (164) | 184–186° C. |
| (58) | 214° C. | (165) | 188–190° C. |
| (59) | 225° C. | (170) | 181–183° C. |
| (60) | 160° C. | (171) | 207–207.5° C. |
| (61) | 147° C. | (172) | 187–188.5° C. |
| (62) | 197° C. | (173) | 201–202° C. |
| (63) | 148° C. | (174) | 127–129° C. |
| (64) | 168° C. | (175) | 135–137° C. |

-continued

| Comp. No. | Melt. pnt. | Comp. No. | Melt. pnt. |
|---|---|---|---|
| (65) | 205° C. | (180) | 125–130° C. |
| (66) | 194° C. | (181) | 135–138° C. |
| (67) | 190–193° C. | (182) | 174° C. |
| (69) | 147° C. | (183) | 190° C. |
| (70) | 157–161° C. | (189) | 163° C. |
| (71) | 219° C. | (190) | 186° C. |
| (72) | 195° C. | (191) | 217° C. |
| (73) | 198° C. | (192) | 213° C. |
| (74) | 206° C. | (196) | 199–203° C. |
| (75) | 193° C. | (197) | 187–188° C. |
| (76) | 182° C. | (198) | 196–200° C. |
| (77) | 227° C. | (199) | 198–202° C. |
| (78) | 213° C. | (200) | 169–173° C. |
| (79) | 211° C. | (201) | 161–164° C. |
| (80) | 217° C. | (202) | 203–207° C. |
| (81) | 230° C. | (203) | 160–163° C. |
| (82) | 235° C. | (204) | 150–153° C. |
| (83) | 250° C. | (205) | 171–173° C. |
| (84) | 222° C. | (206) | 194–197° C. |
| (85) | 244° C. | (207) | 202–207° C. |
| (86) | 255° C. | (208) | 202–206° C. |
| (87) | 228° C. | (209) | 176° C. |
| (88) | 248° C. | (210) | 198° C. |
| (89) | 185° C. | (211) | 186° C. |
| (90) | 208° C. | (212) | 205° C. |
| (91) | 218° C. | (213) | 191° C. |
| (92) | 225° C. | (214) | 203° C. |
| (93) | 211° C. | (215) | 187° C. |
| (94) | 239° C. | (216) | 190° C. |
| (95) | 190° C. | (217) | 204° C. |
| (96) | 211° C. | (218) | 177° C. |
| (101) | 165° C. | (219) | 203° C. |
| (102) | 158–160° C. | (220) | 172° C. |
| (103) | 180–181° C. | (221) | 174° C. |
| (104) | 185–186° C. | (222) | 196° C. |
| (105) | 146–148° C. | (223) | 146° C. |
| (106) | 173–174° C. | | |

When a melting point is stated this has been determined on the "Kofler bank"; a melting range is determined in a melting point bath.

EXAMPLE 2

Preparation of N-(2,6-dichlorobenzoyl)-N'-[4-(1-phenylheptyloxy)phenyl]urea (100)

0.24 g of 55% sodium hydride dispersion in mineral oil were added to a solution of 1.63 g of N-(2,6-dichlorobenzoyl)-N'-(4-hydroxyphenyl)urea in 15 ml of dimethylformamide; the reaction mixture was stirred for 20 minutes with external cooling with water until a bright solution was obtained. 1.6 ml of 77% 1-phenylheptylbromide were added to this solution after which the reaction mixture was left to stand at room temperature for approximately 2 days. After pouring the reaction mixture on a mixture of ice water and petroleum ether a crystalline product was obtained which was sucked off, washed with successively water and little isopropanol and dried in air. The desired product was obtained in a yield of 0.87 g; melting point 146°–149° C. The product was identified by means of its NMR spectrum. The following compounds were prepared in a corresponding manner:

| Comp. No. | Melt. pnt. | Comp. No. | Melt. pnt. |
|---|---|---|---|
| (28) | 138–144° C. | (30) | 138–143° C. |
| (29) | 158–160° C. | | |

In a corresponding manner, in which, however, anhydrous potassium carbonate was used as a base and acetone as a solvent, N-(2-chlorobenzoyl)-N'-[3-chloro-4-(1-phenylpropoxy)phenyl]urea (47) was obtained; melting points 163° C.

EXAMPLE 3

Preparation of N-(2-bromobenzoyl)-N'-[4-(1-phenylethoxy)phenyl]urea (97)

1.0 g of 50% sodium hydride dispersion in mineral oil was added at room temperature to a solution of 4.0 g of 2-bromobenzoyl amide in 25 ml of dry acetonitrile. After stirring for approximately 30 minutes at room temperature, 4.78 g of 4-(1-phenylethoxy)phenylisocyanate were added, the reaction mixture becoming warm and substantially homogeneous. After stirring for another approximately 16 hours at room temperature the reaction mixture was filtered. The filtrate was acidified with dilute hydrochloric acid. The resulting precipitate was sucked off and washed successively with acetonitrile, ethanol and petroleum ether (40–60). The desired product was obtained in a yield of 1.85 g; the melting point was determined on a "Kofler bank" and was 155.5° C.

The following compounds were prepared in a corresponding manner:

| Comp. No. | Melt. pnt. | Comp. No. | Melt. pnt. |
|---|---|---|---|
| (98) | 185° C. | (145) | 156–157° C. |
| (99) | 105° C. | (188) | 197–200° C. |
| (142) | 171° C. | (193) | 172–174.5° C. |
| (143) | 207° C. | (194) | 149–152° C. |
| (144) | oil | (195) | 187–189° C. |

EXAMPLE 4

Preparation of N-(2-chlorobenzoyl)-N'-[4-(1-phenyl-2-hydroxypropoxy)phenyl]urea (114)

A solution of 0.1 g of sodiumborohydride in a mixture of 0.5 ml of water and 0.1 ml of 2 N sodium hydroxide solution was added to a suspension of 1.55 g of N-(2-chlorobenzoyl)-N'-[4-(α-acetylbenzyloxy)phenyl]urea obtained according to the method described in example 1, in 20 ml of ethanol. After stirring for another hour at room temperature the precipitate was sucked off, washed with ethanol and dried; 0.91 g of the desired product was obtained with a melting range of 142°–144° C.

The following compounds were prepared in a corresponding manner

| Comp. No. | Melt. pnt. | Comp. No. | Melt. pnt. |
|---|---|---|---|
| (68) | 158–161° C. | (115) | 153–155° C. |

EXAMPLE 5

Preparation of N-(2-chlorobenzoyl)-N'-[4-(1-phenylethylsulphonyl)phenyl]urea (176)

4.5 g of N-(2-chlorobenzoyl)-N'-[4-(1-phenylethylthio)phenyl]urea obtained according to the method described in example 1 were suspended in 100 ml of acetic acid. After the addition of 7 ml of 40% hydrogen-peroxide solution the reaction mixture was heated on a steam bath for 3 hours. After pouring in water the precipitate was sucked off, washed with acetonitrile and then dissolved in methylene chloride. After filtering off, the solvent was evaporated in which 1.9 g of the desired product were obtained; melting point 226° C.

The following compounds were prepared in a corresponding manner:

| Comp. No. | Melt. pnt. | Comp. No. | Melt. pnt. |
|---|---|---|---|
| (166) | 203–204° C. | (177) | 241° C. |
| (167) | 223–224° C. | (178) | 208–210° C. |
| (168) | 228–230° C. | (179) | 214–216° C. |
| (169) | 224–225° C. | | |

EXAMPLE 6

Preparation of N-(2-chlorobenzoyl)-N'-[4-(α-cyanobenzylimino)-phenyl]urea (184)

2.9 g of N-(2-chlorobenzoyl)-N'-(4-aminophenyl)urea obtained according to the method described in example 1, 1.33 g of 1-phenyl-1-hydroxy acetonitrile and 250 mg of potassium acetate were brought in approximately 25 ml of ethanol, after which the reaction mixture was refluxed for 4 hours. After cooling, the precipitate was sucked off, washed successively with a mixture of ethanol and water (1:1 v/v), ethanol and diisopropyl ether, and finally dried. After recrystallization from acetonitrile, 1.6 g of the desired product were obtained.

Because the determination of the melting point of the product proved to be difficult, the substance was identified by means of N.M.R. and I.R. spectroscopy.

Compound number (185) was prepared in a corresponding manner.

EXAMPLE 7

Preparation of N-(2,6-difluorobenzoyl)-N'-(4-benzilideneaminophenyl-)urea. (187)

2.91 g of N-(2,6-difluorobenzoyl)-N'-(4-aminophenyl-)urea obtained according to the method described in example 1, and 1.41 g of p-chlorobenzaldehyde were refluxed overnight in 50 ml of dry acetonitrile. After cooling, the precipitate was sucked off, washed successively with acetonitrile and diisopropyl ether, and dried. The yield of desired product was 3.2 g; melting point 240° C.

Compound number (186) was prepared in a corresponding manner; melting range 230°–231° C.

EXAMPLE 8

The compositions of the invention are prepared by suspending the compounds in water in the presence of a dispersing agent, for example, lignin sulphonate, and/or a wetting agent, for example naphthalene sulphonate, an alkylsulfphate, an alkylbenzenesulphonate, and alkylpolyoxyethylene or an alkylarylpolyoxyethylene. Young plants of Brussels sprouts, approximately 15 cm high, are sprayed with the compositions thus obtained in various concentrations. After the plants have dried up they are placed in transparent plastic cylinders and then infected with 5 larvae of *Pieris brassicae* (caterpillars of the cabbage white butterfly). The cylinders are then covered with a gauze and stored, an alternating light-dark cycle of 18 hours light and 6 hours dark being used; temperature in the light 24° C., relative humidity (RV) 70%, temperature in the dark 19° C., 80–90% RV. After 5 days the mortality percentage of the larvae is established. Each experiment is carried out threefold. The results of the experiments are stated in the Table A below. The meanings of the symbols stated in the table are as follows:

+ = 90–100% mortality
± = 50–90% mortality
− = <50 mortality.

TABLE A

Insecticidal activity against larvae of *Pieris brassicae* activity; conc. in mg of active subst. per liter

| Comp. Nr. | 300 | 100 | 30 | 10 | 3 | 1 | 0.3 | 0.1 | 0.03 |
|---|---|---|---|---|---|---|---|---|---|
| (1) | + | + | + | + | + | + | + | + | − |
| (2) | + | + | + | + | + | + | + | + | − |
| (3) | + | + | + | + | + | + | + | + | + |
| (4) | + | + | + | + | + | + | + | + | ± |
| (5) | + | + | + | + | + | + | + | | |
| (6) | + | + | + | + | + | | | | |
| (7) | + | + | + | + | + | + | + | + | ± |
| (8) | + | + | + | + | + | + | + | + | − |
| (9) | + | + | + | + | + | + | + | ± | − |
| (10) | + | + | + | + | + | + | ± | | |
| (11) | + | + | + | + | + | + | + | ± | − |
| (12) | + | + | + | + | + | | | | |
| (13) | + | + | + | + | + | + | + | | |
| (14) | + | + | + | + | + | + | + | + | ± |
| (15) | + | + | + | + | + | | | | |
| (16) | + | + | + | + | + | | | | |
| (17) | + | + | + | | | | | | |
| (18) | + | + | + | + | + | | | | |
| (19) | + | + | + | + | + | + | + | | |
| (20) | + | + | + | + | + | ± | − | | |
| (21) | + | + | + | + | + | + | + | ± | − |
| (22) | + | + | + | + | + | | | | |
| (23) | + | + | + | + | + | | | | |
| (24) | + | + | + | + | + | + | + | | |
| (25) | + | + | + | + | + | + | + | | |
| (26) | + | + | + | + | + | | | | |
| (27) | + | + | + | + | + | + | + | | |
| (28) | + | + | + | + | + | | | | |
| (29) | + | + | + | | | | | | |
| (30) | + | + | + | + | + | | | | |
| (31) | + | + | + | + | + | + | ± | ± | − |
| (32) | + | + | + | + | + | + | + | + | − |
| (33) | + | + | + | + | + | + | + | ± | − |
| (34) | + | + | + | + | + | | | | |
| (35) | + | + | + | + | + | + | + | ± | − |
| (36) | + | + | + | + | + | + | + | + | − |
| (37) | + | + | + | | | | | | |
| (38) | + | + | + | + | + | + | + | | |
| (39) | + | + | + | + | + | | | | |
| (40) | + | + | + | + | + | | | | |
| (41) | + | + | + | + | + | + | + | | |
| (42) | + | + | + | | | | | | |
| (43) | + | + | + | | | | | | |
| (44) | + | + | + | + | + | + | + | | |
| (45) | + | + | + | + | + | + | | | |
| (46) | + | + | + | | | | | | |
| (47) | + | + | + | + | + | + | + | + | − |
| (48) | + | + | + | + | + | + | ± | − | |
| (49) | + | + | + | + | ± | − | | | |
| (50) | + | + | + | + | − | | | | |
| (51) | + | + | + | | | | | | |
| (52) | + | + | + | | | | | | |
| (53) | + | + | + | | | | | | |
| (54) | + | + | + | | | | | | |
| (55) | + | + | + | + | + | | | | |
| (56) | + | + | + | + | − | | | | |
| (57) | + | + | + | + | ± | − | | | |
| (58) | + | + | + | + | + | | | | |
| (59) | + | + | + | + | + | | | | |
| (60) | + | + | + | + | + | | | | |
| (61) | + | + | + | | | | | | |
| (62) | + | + | + | + | + | | | | |
| (63) | + | + | + | | | | | | |
| (64) | + | + | + | | | | | | |
| (65) | + | + | + | + | + | + | ± | | |
| (66) | + | + | + | | | | | | |
| (67) | + | + | + | + | + | | | | |
| (68) | + | + | + | + | + | | | | |

TABLE A-continued

Insecticidal activity against larvae of *Pieris brassicae*
activity; conc. in mg of active subst. per liter

| Comp. Nr. | 300 | 100 | 30 | 10 | 3 | 1 | 0.3 | 0.1 | 0.03 |
|---|---|---|---|---|---|---|---|---|---|
| (69) | + | + | + | ± | + | + | + | − | |
| (70) | + | + | + | + | + | + | + | | |
| (71) | + | + | + | − | | | | | |
| (72) | − | | | | | | | | |
| (73) | + | + | + | | | | | | |
| (74) | + | | | | | | | | |
| (75) | + | | | | | | | | |
| (76) | + | | | | | | | | |
| (77) | + | + | + | ± | − | | | | |
| (78) | + | | | | | | | | |
| (79) | + | | | | | | | | |
| (80) | + | + | + | − | | | | | |
| (81) | + | + | + | + | − | | | | |
| (82) | + | − | | | | | | | |
| (83) | + | + | + | + | − | | | | |
| (84) | + | ± | − | | | | | | |
| (85) | + | | | | | | | | |
| (86) | ± | − | | | | | | | |
| (87) | + | − | | | | | | | |
| (88) | + | + | ± | − | | | | | |
| (97) | + | + | + | + | + | | | | |
| (98) | + | + | + | | | | | | |
| (99) | + | + | + | + | + | | | | |
| (100) | + | + | + | + | + | − | | | |
| (101) | + | | | | | | | | |
| (102) | + | | | | | | | | |
| (109) | + | | | | | | | | |
| (110) | − | | | | | | | | |
| (111) | + | + | + | − | | | | | |
| (112) | + | | | | | | | | |
| (113) | + | | | | | | | | |
| (114) | + | | | | | | | | |
| (115) | + | | | | | | | | |
| (116) | + | + | + | ± | − | | | | |
| (117) | + | + | + | + | + | + | + | − | |
| (118) | + | | | | | | | | |
| (119) | + | | | | | | | | |
| (120) | + | | | | | | | | |
| (121) | + | + | + | + | + | | | | |
| (122) | + | + | + | | | | | | |
| (123) | + | | | | | | | | |
| (124) | + | + | + | + | + | | | | |
| (125) | + | | | | | | | | |
| (126) | + | + | + | | | | | | |
| (127) | + | + | + | + | + | | | | |
| (128) | + | | | | | | | | |
| (129) | + | | | | | | | | |
| (130) | + | + | + | + | + | | | | |
| (134) | + | | | | | | | | |
| (135) | − | | | | | | | | |
| (136) | + | | | | | | | | |
| (137) | ± | ± | − | | | | | | |
| (138) | + | | | | | | | | |
| (139) | + | + | + | + | + | | | | |
| (140) | + | | | | | | | | |
| (141) | + | + | + | + | + | | | | |
| (142) | + | + | + | + | + | | | | |
| (143) | + | + | + | + | + | + | + | | |
| (144) | + | + | + | + | + | − | | | |
| (145) | + | + | + | + | + | | | | |
| (146) | + | + | + | + | + | ± | − | | |
| (147) | + | + | − | | | | | | |
| (148) | + | + | + | + | + | + | ± | − | |
| (151) | + | + | + | + | + | + | + | | |
| (155) | + | + | + | + | + | | | | |
| (164) | ± | | | | | | | | |
| (165) | + | | | | | | | | |
| (168) | + | | | | | | | | |
| (169) | + | | | | | | | | |
| (183) | + | + | + | | | | | | |
| (188) | + | + | + | + | + | | | | |
| (189) | + | + | + | + | + | ± | − | | |
| (190) | + | + | + | + | + | + | ± | − | |
| (191) | + | + | + | + | ± | − | | | |
| (192) | + | + | + | + | + | − | | | |

EXAMPLE 9

20 Larvae of *Aedes aegypts* (larvae of the yellow fever mosquito) were brought in aqueous suspensions of the active substances in various concentrations obtained according to Example 8. These suspensions are maintained at a temperature of 25° C. for 10 days, during which incubation period the larvae are fed with an aqueous suspension of powdered brown bread and yeast. The mortality percentage is determined after 10 days taking into account the natural mortality. The results of the experiment are recorded in table B. The meanings of the symbols are the same as in example 8.

TABLE B

Insecticidal activity against larvae of *Aedes aegypti*
activity; conc. in mg of active subst. per liter

| Comp. Nr. | 1 | 0.3 | 0.1 | 0.03 | 0.01 | 0.003 | 0.001 |
|---|---|---|---|---|---|---|---|
| (1) | + | + | + | + | + | ± | − |
| (2) | + | + | + | + | + | − | |
| (3) | + | + | + | + | + | + | − |
| (4) | + | + | + | + | − | | |
| (5) | + | + | + | + | + | | |
| (7) | + | + | + | + | + | ± | − |
| (8) | + | + | + | + | − | | |
| (9) | + | + | + | + | − | | |
| (10) | + | + | + | | | | |
| (11) | + | + | + | + | + | | |
| (12) | + | + | + | | | | |
| (13) | + | + | + | + | + | | |
| (14) | + | + | + | + | − | | |
| (15) | + | + | + | | | | |
| (16) | + | + | + | ± | ± | | |
| (18) | + | + | + | + | + | | |
| (19) | + | + | + | + | ± | | |
| (21) | + | + | + | + | + | + | − |
| (22) | + | + | + | | | | |
| (24) | + | + | + | + | + | | |
| (27) | + | + | + | + | + | | |
| (29) | + | + | + | | | | |
| (30) | + | + | ± | | | | |
| (31) | + | + | − | | | | |
| (32) | + | + | + | + | + | + | − |
| (33) | + | + | + | + | + | | |
| (34) | + | + | + | + | + | | |
| (35) | + | + | − | | | | |
| (36) | + | + | + | + | + | + | − |
| (38) | + | + | + | + | + | | |
| (40) | + | + | + | | | | |
| (41) | + | + | + | + | + | | |
| (42) | + | + | + | | | | |
| (43) | ± | ± | − | | | | |
| (44) | + | + | + | | | | |
| (45) | + | + | + | + | + | | |
| (46) | + | + | + | | | | |
| (47) | + | + | + | + | + | ± | − |
| (51) | + | + | − | | | | |
| (55) | + | + | ± | ± | − | | |
| (58) | + | + | + | ± | ± | | |
| (59) | + | + | ± | − | | | |
| (62) | + | | | | | | |
| (63) | + | + | + | | | | |
| (64) | + | − | | | | | |
| (65) | + | + | + | | | | |
| (66) | ± | − | | | | | |
| (67) | + | | | | | | |
| (68) | + | + | + | − | | | |
| (70) | + | + | + | + | ± | | |
| (71) | + | + | + | + | + | − | |
| (72) | + | ± | ± | − | | | |
| (81) | + | + | + | + | − | | |
| (97) | + | + | + | ± | − | | |
| (98) | ± | − | | | | | |
| (99) | + | + | + | + | + | | |
| (100) | + | + | + | + | − | | |
| (102) | + | | | | | | |
| (109) | + | | | | | | |
| (110) | + | + | − | | | | |
| (111) | + | + | − | | | | |

TABLE B-continued

Insecticidal activity against larvae of *Aedes aegypti*
activity; conc. in mg of active subst. per liter

| Comp. Nr. | 1 | 0.3 | 0.1 | 0.03 | 0.01 | 0.003 | 0.001 |
|---|---|---|---|---|---|---|---|
| (113) | + | | | | | | |
| (114) | ± | | | | | | |
| (117) | + | − | | | | | |
| (121) | + | + | ± | − | | | |
| (124) | + | + | ± | ± | − | | |
| (127) | + | + | + | ± | − | | |
| (128) | + | | | | | | |
| (130) | + | + | + | + | ± | | |
| (134) | + | | | | | | |
| (135) | + | + | + | − | | | |
| (136) | + | | | | | | |
| (137) | + | + | + | − | | | |
| (139) | + | + | + | ± | − | | |
| (142) | + | + | ± | − | | | |
| (143) | + | + | + | + | − | | |
| (148) | + | + | + | + | − | | |
| (155) | + | + | + | − | | | |
| (164) | ± | | | | | | |
| (165) | + | | | | | | |
| (169) | + | | | | | | |
| (183) | + | + | + | | | | |
| (188) | ± | | | | | | |
| (190) | + | + | + | + | − | | |
| (192) | + | + | + | + | + | + | + |

EXAMPLE 10

Young potato plants, approximately 15 cm high, are sprayed with the compositions obtained according to example 8 in various concentrations. After the plants have dried up, cylinders of transparent plastics are placed over the plants. The plants are then infected with 10 larvae of *Leptinotarsa decemlineata* (larvae of the colorado beetle) and stored as indicated in example 8. After 5 days the mortality percentage of the larvae is established. The results of the experiment are recorded in table C below. The meanings of the symbols are the same as in example 8.

TABLE C

Insecticidal activity against larvae of *Leptinotarsa decemlineata*
activity; conc. in mg of active subst. per liter

| Comp. Nr. | 300 | 100 | 30 | 10 | 3 | 1 | 0.3 | 0.1 |
|---|---|---|---|---|---|---|---|---|
| (1) | + | + | + | + | + | + | − | |
| (2) | + | + | + | + | + | ± | − | |
| (3) | + | + | + | + | + | − | | |
| (4) | + | + | + | + | + | − | | |
| (5) | + | + | + | + | − | | | |
| (6) | + | + | ± | | | | | |
| (7) | + | + | + | + | + | ± | − | |
| (8) | + | + | + | + | ± | ± | − | |
| (9) | + | + | + | + | ± | − | | |
| (10) | + | + | + | + | − | | | |
| (11) | + | + | + | + | + | ± | − | |
| (12) | + | + | + | + | + | | | |
| (13) | + | + | + | + | + | ± | − | |
| (14) | + | + | + | + | ± | − | | |
| (15) | + | + | + | + | + | | | |
| (16) | + | + | + | + | ± | | | |
| (17) | + | + | + | | | | | |
| (18) | + | + | + | + | + | | | |
| (20) | + | ± | ± | ± | − | | | |
| (21) | + | + | + | + | + | + | ± | − |
| (22) | + | + | + | + | + | | | |
| (23) | + | + | + | | | | | |
| (24) | + | + | + | + | + | ± | | |
| (25) | + | + | + | ± | ± | − | | |
| (26) | + | + | + | + | − | | | |
| (27) | + | + | + | + | + | ± | − | |
| (28) | + | + | + | | | | | |
| (30) | + | + | + | ± | − | | | |
| (31) | + | + | − | | | | | |
| (32) | + | + | ± | ± | − | | | |
| (33) | + | + | ± | − | | | | |
| (34) | + | + | + | ± | − | | | |
| (35) | + | + | − | | | | | |
| (36) | ± | ± | − | | | | | |
| (37) | + | + | + | | | | | |
| (38) | + | + | + | + | + | − | | |
| (39) | + | + | + | ± | − | | | |
| (40) | ± | ± | ± | − | | | | |
| (41) | + | + | + | + | + | + | − | |
| (42) | + | + | + | | | | | |
| (43) | + | + | + | | | | | |
| (44) | + | + | + | + | + | + | − | |
| (45) | + | + | + | + | + | + | − | |
| (46) | + | + | + | | | | | |
| (47) | + | + | + | + | + | + | − | |
| (48) | + | + | + | ± | − | | | |
| (49) | ± | ± | | | | | | |
| (51) | + | ± | − | | | | | |
| (57) | ± | − | | | | | | |
| (60) | ± | ± | ± | − | | | | |
| (61) | + | + | + | | | | | |
| (62) | + | + | + | ± | − | | | |
| (63) | + | + | + | | | | | |
| (64) | + | + | ± | | | | | |
| (65) | + | + | + | + | − | | | |
| (68) | + | + | + | − | | | | |
| (69) | ± | − | | | | | | |
| (70) | + | ± | − | | | | | |
| (73) | + | ± | − | | | | | |
| (76) | ± | | | | | | | |
| (80) | ± | − | | | | | | |
| (97) | + | + | + | + | ± | | | |
| (98) | + | ± | ± | | | | | |
| (99) | + | + | + | + | + | | | |
| (100) | ± | ± | − | | | | | |
| (102) | + | | | | | | | |
| (113) | + | | | | | | | |
| (114) | + | | | | | | | |
| (117) | + | − | | | | | | |
| (124) | + | + | + | ± | | | | |
| (129) | ± | | | | | | | |
| (130) | + | + | + | + | ± | | | |
| (134) | ± | | | | | | | |
| (135) | ± | − | | | | | | |
| (136) | + | − | | | | | | |
| (137) | + | + | + | − | | | | |
| (139) | + | + | + | + | − | | | |
| (142) | + | + | + | | | | | |
| (144) | + | + | − | | | | | |
| (145) | + | ± | ± | | | | | |
| (148) | + | ± | − | | | | | |
| (151) | + | + | + | ± | ± | − | | |
| (155) | + | + | ± | − | | | | |
| (169) | ± | | | | | | | |
| (188) | + | + | ± | − | | | | |
| (189) | ± | − | | | | | | |
| (190) | + | ± | ± | − | | | | |
| (192) | + | ± | ± | ± | − | | | |

What is claimed is:

1. A compound of the formula:

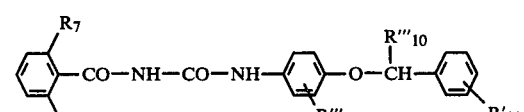

wherein
R7 and R8 either are both fluorine or R7 is a hydrogen atom and R8 is a chlorine atom or a methyl group;

$R_9'''$ is a hydrogen atom or 1 or 2 methyl groups in the 3- or 3,5-positions with respect to the NH-function;

$R_{10}'''$ is an alkyl group having 1 to 4 carbon atoms, an alkenyl group having 1 to 4 carbon atoms, or trifluoromethyl, and $R_{12}'$ is a hydrogen atom or a substituent in the 3- and/or 4-position(s) selected from the group consisting of a halogen atom, a methyl group, and a halomethyl group.

2. N-(2,6-difluorobenzoyl)-N'-[4-(1-phenylethoxy)-phenyl]urea.

3. N-(2-chlorobenzoyl)-N'-[4-(1-phenylethoxy)-phenyl]urea.

4. N-(2,6-difluorobenzoyl)-N'-[4-(1-phenylbutoxy)-phenyl]urea.

5. N-(2-chlorobenzoyl)-N'[4-(1-phenylbutoxy)-phenyl]urea.

6. N-(2,6-difluorobenzoyl)-N'-[4-(1-phenylpropoxy)-phenyl]urea.

7. N-(2-chlorobenzoyl)-N'-[4-(1-phenylpropoxy)-phenyl]urea.

8. N-(2-methylbenzoyl)-N'-[4-(1-phenylpropoxy)-phenyl]urea.

9. N-(2-chlorobenzoyl)-N'-[4-(1-phenylbenzyloxy)-phenyl]urea.

10. N-(2,6-difluorobenzoyl)-N'-[4-(1-phenylbenzyloxy)phenyl]urea.

11. N-(2,6-difluorobenzoyl)-N'-[4-{1-(4-chlorophenyl)ethoxy}phenyl]urea.

12. N-(2,6-difluorobenzoyl)-N'-(4-benzyloxyphenyl)urea.

13. N-(2-chlorobenzoyl)-N'-(3,5-dimethyl-4-benzyloxyphenyl)urea.

14. N-(2,6-difluorobenzoyl)-N'-(3,5-dimethyl)-4-benzyloxyphenyl)urea.

15. An insecticidal composition comprising
an insecticidally effective amount of a compound of the formula:

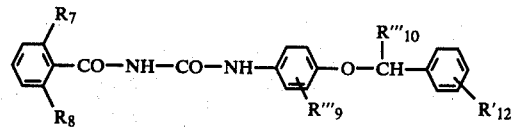

wherein $R_7$ and $R_8$ either are both fluorine or $R_7$ is a hydrogen atom and $R_8$ is a chlorine atom or a methyl group;

$R_9'''$ is a hydrogen atom or 1 or 2 methyl groups in the 3- or, 3,5,-positions with respect to the NH-function;

$R_{10}'''$ is an alkyl group having 1 to 4 carbon atoms, an alkenyl group having 1 to 4 carbon atoms, or trifluoromethyl, and $R_{12}'$ is a hydrogen atom or a substituent in the 3- and/or 4-position(s) selected from the group consisting of a halogen atom, a methyl group, and a halomethyl group, and a liquid or solid inert carrier material.

16. A composition as claimed in claim 15, characterized in that the active constituent is N-(2,6-difluorobenzoyl)-N'-[4-(1-phenylethoxy)phenyl]urea.

17. A composition as claimed in claim 15, characterized in that the active constituent is N-(2-chlorobenzoyl)-N'-[4-(1-phenylethoxy)phenyl]urea.

18. A composition as claimed in claim 15, characterized in that the active constituent is N-(2,6-difluorobenzoyl)-N'-[4-(1-phenylbutoxy)phenyl]urea.

19. A composition as claimed in claim 15, characterized in that the active constituent is N-(2-chlorobenzoyl)-N'-[4-(1phenylbutoxy)phenyl]urea.

20. A composition as claimed in claim 15, characterized in that the active constituent is N-(2,6-difluorobenzoyl)-N'-[4-(1-phenylpropoxy)phenyl]urea.

21. A composition as claimed in claim 15, characterized in that the active constituent is N-(2-chlorobenzoyl)-N'-[4-(1-phenylpropoxy)phenyl]urea.

22. A composition as claimed in claim 15, characterized in that the active constituent is N-(2-methylbenzoyl)-N'-[4-(1-phenylpropoxy)phenyl]urea.

23. A composition as claimed in claim 15, characterized in that the active constituent is N-(2-chlorobenzoyl)-N'-[4-(1-phenylbenzyloxy)phenyl]urea.

24. A composition as claimed in claim 15, characterized in that the active constituent is N-(2,6-difluorobenzoyl)-N'-[4-(1-phenylbenzyloxy)phenyl]urea.

25. A composition as claimed in claim 15, characterized in that the active constituent is N-(2,6-difluorobenzoyl)-N'-[4-{1-(4-chlorophenyl)ethoxy}phenyl]urea.

26. A composition as claimed in claim 15, characterized in that the active constituent is N-(2,6-difluorobenzoyl)-N'-(4-benzyloxyphenyl)urea.

27. A composition as claimed in claim 15, characterized in that the active constituent is N-(2-chlorobenzoyl)-N'-(3,5-dimethyl-4-benzyloxyphenyl)urea.

28. A composition as claimed in claim 15, characterized in that the active constituent is N-(2,6-difluorobenzoyl)-N'-(3,5-dimethyl-4-benzyloxyphenyl)urea.

29. A method of controlling insects, characterized in that the infested area is treated with a composition as claimed in any of the claims 15 to 28 in a dosage from 10 to 5000 g of active substance per hectare.

30. An insecticidal composition comprising
an insecticidally effective amount of a compound selected from the group consisting of
N-(2,6-difluorobenzoyl)-$N^1$-[4-(1-phenylethoxy)phenyl] area,
N-(2-chlorobenzoyl)-$N^1$-[4-(1-phenylethoxy) phenyl] area,
N-(2,6-difluorobenzoyl)-$N^1$-[4-(1-phenylbutoxy)phenyl] area,
N-(2-chlorobenzoyl)-$N^1$-[4-(1-phenylbutoxy)phenyl] area,
N-(2,6-difluorobenzoyl)-$N^1$-[4-(1-phenylpropoxy)phenyl] area,
N-(2-chlorobenzoyl)-$N^1$-[4-(1-phenylproxy)phenyl] area,
N-(2-methylbenzoyl)-$N^1$-[4-(1-phenylpropoxy)phenyl] area,
N-(2-chlorobenzoyl)-$N^1$-[4-(1-phenylbenzoyloxy)phenyl] area,
N-(2,6-difluorobenzoyl)-$N^1$-[4-(1-phenylbenzyloxy)phenyl] area,
N-(2,6-difluorobenzoyl)-$N^1$-(4-benzyloxyphenyl) area,
N-(2-chlorobenzoyl)-$N^1$-(3,5-dimethyl-4-benzyloxyphenyl) area, and
N-(2,6-difluorobenzoyl)-$N^1$-(3,5-dimethyl-4-benzyloxyphenyl) area and
a liquid or solid inert carrier material.

* * * * *